United States Patent
Lee et al.

(10) Patent No.: US 10,584,338 B2
(45) Date of Patent: Mar. 10, 2020

(54) PROMOTER AND USE THEREOF

(71) Applicant: CJ CHEILJEDANG CORPORATION, Seoul (KR)

(72) Inventors: Young Mi Lee, Suwon-si (KR); Seung Bin Lee, Suwon-si (KR); Seong Bo Kim, Seongnam-si (KR); Ji Hyun Lee, Suwon-si (KR); Seung Hyun Cho, Seoul (KR); Seung Won Park, Yongin-si (KR); Jin Sook Chang, Suwon-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 16/327,581

(22) PCT Filed: Mar. 20, 2017

(86) PCT No.: PCT/KR2017/002964
§ 371 (c)(1),
(2) Date: Feb. 22, 2019

(87) PCT Pub. No.: WO2018/043856
PCT Pub. Date: Mar. 8, 2018

(65) Prior Publication Data
US 2019/0185857 A1    Jun. 20, 2019

(30) Foreign Application Priority Data
Aug. 31, 2016 (KR) ........................ 10-2016-0111810

(51) Int. Cl.
| | | |
|---|---|---|
| C07H 21/04 | (2006.01) |
| C12N 15/70 | (2006.01) |
| C12N 1/21 | (2006.01) |
| C12N 9/02 | (2006.01) |
| C12N 9/92 | (2006.01) |
| C12P 19/02 | (2006.01) |
| C12N 15/113 | (2010.01) |
| C12P 19/24 | (2006.01) |
| C12N 1/20 | (2006.01) |
| C12N 9/90 | (2006.01) |
| C12N 15/77 | (2006.01) |

(52) U.S. Cl.
CPC ............. *C12N 15/113* (2013.01); *C12N 1/20* (2013.01); *C12N 9/90* (2013.01); *C12N 15/77* (2013.01); *C12P 19/02* (2013.01); *C12P 19/24* (2013.01)

(58) Field of Classification Search
CPC .......... C12N 15/52; C12N 15/70; C12N 9/90; C12N 1/20; C12N 15/77; C12N 15/74; C12P 19/02; C12P 19/24; C12Y 501/03; C07H 21/04
USPC ................. 435/158, 106, 320.1, 233, 252.2; 536/23.2
See application file for complete search history.

(56) References Cited

FOREIGN PATENT DOCUMENTS

| KR | 2006-0068505 A | 6/2006 |
| KR | 2008-0025355 A | 3/2008 |
| KR | 2011-0101010 A | 9/2011 |
| KR | 2014-0066553 A | 6/2014 |
| KR | 2014-0110134 A | 9/2014 |
| KR | 2015-0001341 A | 1/2015 |
| KR | 10-1632642 B1 | 6/2016 |

OTHER PUBLICATIONS

Eikmanns et al., "A family of *Corynebacterium glutamicum / Escherichia coli* shuttle vectors for cloning, controlled gene expression, and promoter probing," *Gene* 102:93-98 (1991).
GenBank: CP005959.1, "Corynebacterium glutamicum MB001, complete genome," (470 pages) (Jan. 30, 2014).
Paik et al., "Isolation of transcription initiation signals from *Corynebacterium ammoniagenes* and comparison of their gene expression levels in *C. ammoniagenes* and *Escherichia coli*," *Biotechnology Letters* 25:1311-1316 (2003).
Van Der Rest et al., "A heat shock following electroporation induces highly efficient transformation of *Corynebacterium glutamicum* with xenogeneic plasmid DNA," *Appl Microbiol Biotechnol* 52:541-545 (1999).

*Primary Examiner* — Robert B Mondesi
*Assistant Examiner* — Mohammad Y Meah
(74) *Attorney, Agent, or Firm* — Seed IP Law Group LLP

(57) ABSTRACT

The present invention relates to a novel promoter, a vector comprising the promoter, a microorganism comprising the promoter or the vector, and a method for producing a target product using the microorganism.

16 Claims, 3 Drawing Sheets

Specification includes a Sequence Listing.

SEQUENCE LISTING

```
<160> NUMBER OF SEQ ID NOS: 25

<210> SEQ ID NO 1
<211> LENGTH: 294
<212> TYPE: DNA
<213> ORGANISM: Artificial Sequence
<220> FEATURE:
<223> OTHER INFORMATION: Synthetic sequence SPL1

<400> SEQUENCE: 1
```

```
ggcgcttcat gtcaacaatc tttaacgttt tcaagttcac aagtcgtgtt caaatggtga      60
caagattgga cactgtgctg aattggcacc aagccctcat aaatgataga tctaaatcga     120
atatcaatat atggtctgtt tattggaacg cgtcccagtg gctgagacgc atccgctaaa     180
gccccaggaa ccctgtgcag aaagaacaaa taatcgtgaa ttttggcagc aacagtgagt     240
cctgatacaa ttgaaaacgt gcaaaagcat aaattattgg aggagatcaa aaca           294

<210> SEQ ID NO 2
<211> LENGTH: 294
<212> TYPE: DNA
<213> ORGANISM: Artificial Sequence
<220> FEATURE:
<223> OTHER INFORMATION: Synthetic sequence SPL7

<400> SEQUENCE: 2
ggcgcttcat gtcaacaatc tttaacgttt tcaagttcac aagtcgtgtt caaatggtga      60
caagattgga cactgtgctg aattggcacc aagccctcat aaatgataga tctaaatcga     120
atatcaatat atggtctgtt tattggaacg cgtcccagtg gctgagacgc atccgctaaa     180
gccccaggaa ccctgtgcag aaagaacaaa taatcgtgaa ttttggcagc aacagcaatt     240
cctgctacaa ttgaaaacgt gcaaaagcat agattattgg aggagatcaa aaca           294

<210> SEQ ID NO 3
<211> LENGTH: 294
<212> TYPE: DNA
<213> ORGANISM: Artificial Sequence
<220> FEATURE:
<223> OTHER INFORMATION: Synthetic sequence SPL13

<400> SEQUENCE: 3
ggcgcttcat gtcaacaatc tttaacgttt tcaagttcac aagtcgtgtt caaatggtga      60
caagattgga cactgtgctg aattggcacc aagccctcat aaatgataga tctaaatcga     120
atatcaatat atggtctgtt tattggaacg cgtcccagtg gctgagacgc atccgctaaa     180
gccccaggaa ccctgtgcag aaagaacaaa taatcgtgaa ttttggcagc aacagcgggg     240
cctggtataa ttgaaaacgt gcaaaagcat agattattgg aggagatcaa aaca           294

<210> SEQ ID NO 4
<211> LENGTH: 26
<212> TYPE: DNA
<213> ORGANISM: Artificial Sequence
<220> FEATURE:
<223> OTHER INFORMATION: SPL primer-1

<400> SEQUENCE: 4
ggtaccggcg cttcatgtca acaatc                                           26

<210> SEQ ID NO 5
<211> LENGTH: 25
<212> TYPE: DNA
<213> ORGANISM: Artificial Sequence
<220> FEATURE:
<223> OTHER INFORMATION: SPL primer-2

<400> SEQUENCE: 5
gatatctgtt ttgatctcct ccaat                                            25

<210> SEQ ID NO 6
<211> LENGTH: 23
<212> TYPE: DNA
<213> ORGANISM: Artificial Sequence
```

```
<220> FEATURE:
<223> OTHER INFORMATION: GFP primer-1

<400> SEQUENCE: 6
gatatcatga gtaaaggaga aga                                              23

<210> SEQ ID NO 7
<211> LENGTH: 23
<212> TYPE: DNA
<213> ORGANISM: Artificial Sequence
<220> FEATURE:
<223> OTHER INFORMATION: GFP primer-2

<400> SEQUENCE: 7
ctgcagttat ttgtagagct cat                                              23

<210> SEQ ID NO 8
<211> LENGTH: 870
<212> TYPE: DNA
<213> ORGANISM: Artificial Sequence
<220> FEATURE:
<223> OTHER INFORMATION: Synthetic sequence pET24-ATPE-2

<400> SEQUENCE: 8
atgaaacacg gcatctatta ttcttactgg gaacatgagt ggagcgccaa gttcggtccc       60
tatatcgaga aggtcgccaa gctcggtttc gacatcctcg aagtcgccgc ccaccatatc      120
aacgaataca gcgacgccga actcgcgacc atcaggaaga gcgcgaagga taacggcatc      180
atcctcaccg ccggcatcgg tccgtcgaaa accaagaacc tgtcgtcgga agatgctgcg      240
gtgcgtgcgg ccggcaaggc gttctttgaa gaaccctttt cgaacgtcgc caagctcgat      300
atccacacca tcggcggcgc attgcattcc tattggccaa tcgattattc gcagcccgtc      360
gacaaggcag gcgattatgc gcgcggcgtc gagggtatca acggcattgc cgatttcgcc      420
aatgatctcg gcatcaacct gtgcatcgaa gtcctcaacc gctttgaaaa ccacgtcctc      480
aacacggcgg cggaaggcgt cgcttttgtg aaggatgtcg gcaagaacaa tgtgaaagtc      540
atgctggata ccttccacat gaacatcgag gaagacagtt tcggtgacgc catccgcacg      600
gccggcccgc ttctggggca cttccatacc ggtgaatgca atcgccgcgt accgggcaag      660
ggcagaatgc cgtggcacga aatcggcctt gcgctgcgtg atatcaacta caccggcgcg      720
gtaatcatgg agccttttcgt caagacaggc ggcaccatcg gctcggatat caaggtgtgg      780
cgcgacctga gcggtggcgc cgacatcgcg aaaatggatg aagatgcccg caatgcgctg      840
gcattctccc gcttcgttct tggtggctga                                      870

<210> SEQ ID NO 9
<211> LENGTH: 42
<212> TYPE: DNA
<213> ORGANISM: Artificial Sequence
<220> FEATURE:
<223> OTHER INFORMATION: ATPE primer-1

<400> SEQUENCE: 9
atctaggaga ttaagatatc atgaaacacg gcatctatta tt                         42

<210> SEQ ID NO 10
<211> LENGTH: 36
<212> TYPE: DNA
<213> ORGANISM: Artificial Sequence
<220> FEATURE:
<223> OTHER INFORMATION: ATPE primer-2
```

<400> SEQUENCE: 10

```
gtggatcccc cgggctgcag tcagccacca agaacg                                36
```

<210> SEQ ID NO 11
<211> LENGTH: 1473
<212> TYPE: DNA
<213> ORGANISM: Artificial Sequence
<220> FEATURE:
<223> OTHER INFORMATION: Synthetic sequence pET28a-TN(m)

<400> SEQUENCE: 11

```
atggtcttga aagtgttcaa agatcacttt ggaaggggat acgaagttta cgaaaagtct      60
tatagagaaa aggattctct ctctttcttc ttgacaaagg gagaggaagg aaaaattctg    120
gtagtggctg agaaaaggc acctgagggt ctgtcgtttt tcaaaaaaca gcgggtggag     180
ggtgtttcgt tcttttttctg tgagagaaat catgagaact tggaagttct cagaaaatac   240
tttccagatc tcaaaccagt tcgagcagga ttgagagcgt cttttggaac aggtgacaga    300
ctcggtatca ccacaccggc tcacgtgagg gcgttgaagg attcagggct tttttcccatc   360
tttgcgcagc aggacgtgag ggagaacgaa agaacgggaa ggacctggag agatgtgctg    420
gacgatgcca catggggagt tttccaggag ggatacagtg agggattcgg agcagacgcc    480
gatcacgcga agcggccgga ggatcttgtt tcggctgcaa gggaaggttt caccatgttc    540
acaatcgatc cttcgaatca tgtgaggaat ctttcaaaac tcagtgaaag agaaaagaac   600
gagatgttcg aggaaatact gaaaaagag cgaatcgaca ggatctatct gggaaaaaa     660
tacaccgtcc tcggtgaaag actggagttc gacgagaaaa atttgaggga tgctgctctg   720
gtgtactatg atgcgatcgc ccacgtggat atgatgtatc aaattttgaa agacgaaacc   780
ccggatatcg acttcgaagt gtcagttgac gaaacagaaa ctcccacgag tcctctcttc   840
cacattttcg ttgtggaaga actcagacga agaggtgtgg agttcaccaa tcttgccctg   900
agattcatcg cgaatgggaa aaagggaata ggttacaagg gggatcttgc acagttcgag   960
agagaaatca aaatgcacgc agaaatcgca aggatgttcg aaggatacaa aatatcactc  1020
cactctggaa gcgacaaatt ttccgtgtat cctgcttttg cttccgcgac aggaggcctt  1080
ttccacgtga agacagccgg aacgagttat cttgaggcgg tgaaggtcat atccatggtc  1140
aacccggagc tcttccggga gatctacagg tgtgctctcg atcactttga ggaagacaga  1200
aagtcctatc acatatctgc ggatctgtcg aaagttccgg aagtagagaa agtgaaagat  1260
gaagatcttc caggtctttt tgaagacatc aacgtgagac agttgatcca tgtcaccctat 1320
ggctctgttc tgaaagatgc atctttgaaa gaacggctgt ttaagacgct tgaacaaaat  1380
gaggaactct tctacgagac cgtggcaaaa catataaaaa ggcacgtaga cctgttgaag  1440
gggtgactcg agcaccacca ccaccaccac tga                                1473
```

<210> SEQ ID NO 12
<211> LENGTH: 28
<212> TYPE: DNA
<213> ORGANISM: Artificial Sequence
<220> FEATURE:
<223> OTHER INFORMATION: TN(m) primer-1

<400> SEQUENCE: 12

```
gatatcatgg tcttgaaagt gttcaaag                                         28
```

<210> SEQ ID NO 13
<211> LENGTH: 30

```
<212> TYPE: DNA
<213> ORGANISM: Artificial Sequence
<220> FEATURE:
<223> OTHER INFORMATION: TN(m) primer-2

<400> SEQUENCE: 13
ctgcagtcac cccttcaaca ggtctacgtg                                      30

<210> SEQ ID NO 14
<211> LENGTH: 36
<212> TYPE: DNA
<213> ORGANISM: Artificial Sequence
<220> FEATURE:
<223> OTHER INFORMATION: vectors pECCG117-CJ7-ilvE sequence

<400> SEQUENCE: 14
gagatcaaaa cagatatcat gacgtcatta gagttc                                36

<210> SEQ ID NO 15
<211> LENGTH: 34
<212> TYPE: DNA
<213> ORGANISM: Artificial Sequence
<220> FEATURE:
<223> OTHER INFORMATION: vector pECCG117-SPL7-ilvE sequence

<400> SEQUENCE: 15
atcccccggg ctgcagttag ccaaccagtg ggta                                  34

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
atcctctaga gtcgaccaaa tgctccaacc gtccgt                                36

<210> SEQ ID NO 17
<211> LENGTH: 26
<212> TYPE: DNA
<213> ORGANISM: Artificial Sequence
<220> FEATURE:
<223> OTHER INFORMATION: Primer sequence

<400> SEQUENCE: 17
ctcgaggaac tcattccttc tgctcg                                           26

<210> SEQ ID NO 18
<211> LENGTH: 38
<212> TYPE: DNA
<213> ORGANISM: Artificial Sequence
<220> FEATURE:
<223> OTHER INFORMATION: Primer sequence

<400> SEQUENCE: 18
tctagaacta gtgggcccga catctaataa ccgggcag                              38

<210> SEQ ID NO 19
<211> LENGTH: 36
<212> TYPE: DNA
<213> ORGANISM: Artificial Sequence
<220> FEATURE:
<223> OTHER INFORMATION: Primer sequence

<400> SEQUENCE: 19
```
atgcctgcag gtcgacgcag acgcactcga ctacac                     36

<210> SEQ ID NO 20
<211> LENGTH: 36
<212> TYPE: DNA
<213> ORGANISM: Artificial Sequence
<220> FEATURE:
<223> OTHER INFORMATION: Primer sequence

<400> SEQUENCE: 20
gaatgagttc ctcgagagaa acatcccagc gctact                     36

<210> SEQ ID NO 21
<211> LENGTH: 36
<212> TYPE: DNA
<213> ORGANISM: Artificial Sequence
<220> FEATURE:
<223> OTHER INFORMATION: Primer sequence

<400> SEQUENCE: 21
gcccactagt tctagattat ttgatatcaa atacga                     36

<210> SEQ ID NO 22
<211> LENGTH: 36
<212> TYPE: DNA
<213> ORGANISM: Artificial Sequence
<220> FEATURE:
<223> OTHER INFORMATION: Primer sequence

<400> SEQUENCE: 22
gaatgagttc ctcgagggcg cttcatgtca acaatc                     36

<210> SEQ ID NO 23
<211> LENGTH: 36
<212> TYPE: DNA
<213> ORGANISM: Artificial Sequence
<220> FEATURE:
<223> OTHER INFORMATION: Primer sequence

<400> SEQUENCE: 23
attgttttgt catatgtgtt ttgatctcct ccaata                     36

<210> SEQ ID NO 24
<211> LENGTH: 23
<212> TYPE: DNA
<213> ORGANISM: Artificial Sequence
<220> FEATURE:
<223> OTHER INFORMATION: Primer sequence

<400> SEQUENCE: 24
catatgacaa aacaatataa aaa                                   23

<210> SEQ ID NO 25
<211> LENGTH: 717
<212> TYPE: DNA
<213> ORGANISM: Artificial Sequence
<220> FEATURE:
<223> OTHER INFORMATION: Synthetic sequence GFP

<400> SEQUENCE: 25
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcccgtt atccggatca tatgaaacgg   240

```
catgactttt tcaagagtgc catgcccgaa ggttatgtac aggaacgcac tatatctttc    300
aaagatgacg ggaactacaa gacgcgtgct gaagtcaagt ttgaaggtga taccctttgtt   360 aatcgtatcg agttaaaagg tattgatttt aaagaagatg gaaacattct cggacacaaa   420
ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct ttcgaaagat cccaacgaaa agcgtgacca catggtcctt   660
cttgagtttg taactgctgc tgggattaca catggcatgg atgagctcta caaataa      717
```

PROMOTER AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_439USPC_SEQUENCE_LISTING.txt. The text file is 9.4 KB, was created on Feb. 20 2019, and is being submitted electronically via EFS-Web.

TECHNICAL FIELD

The present disclosure relates to a novel promoter, a vector comprising the promoter, a microorganism comprising the promoter or vector, and a method for producing a target product using the microorganism.

BACKGROUND ART

Continuous efforts have been made for the production of target products, such as amino acids or useful materials which can be used for various purposes including feeds, pharmaceutical drugs, foods, etc., at high titer using microorganisms (Korean Patent No. 10-0924065). As one of such methods, there is a method for inducing overexpression of a target gene in a microorganism, and a high-efficiency gene expression system is necessary for this purpose. Since promoters are one of the factors which are significantly involved in gene expression systems, development of a useful promoter is essential.

E. coli-derived tac promoter is widely-known as a strong promoter. In the case of the Coryne-form microorganism, strong promoters have been developed by modifying the promoters of self-genes (Gene, 102, 93-98, 1991; Microbiology, 142, 1297-1309, 1996). For example, in the cases of promoters derived from Corynebacterium ammoniagenesis, it is disclosed that there is about 10% improvement compared to that of the tac promoter reported in E. coli (Biotechnol. Lett. 25, 1311-1316, 2003). Additionally, as strong promoters derived from Corynebacterium ammoniagenesis, Pcj1 to Pcj7 promoters with various strengths were developed and they have strong promoter activities with at least 10-fold higher than that of tac promoter (Korean Patent No. 10-0620092). Additionally, the Po2 promoter, which was synthesized from Corynebacterium glutamicum to have a strong promoter activity, was developed (Korean Patent No. 10-1632642). However, there is still a need for the development of a promoter, since a system which exhibits high expression efficiency in Corynebacterium compared to the gene expression system of E. coli is needed.

Under the circumstances, the present inventors have made many efforts to discover promoters that can strongly induce gene expression in a microorganism of the genus Corynebacterium. As a result, they have developed a novel synthesized promoter of the present disclosure and confirmed that the promoter has a higher expression activity compared to those of the known promoters, thereby completing the present disclosure.

DISCLOSURE

Technical Problem

An object of the present disclosure is to provide a novel nucleic acid molecule having promoter activity; a gene expression cassette containing the nucleic acid molecule and a target gene; a recombinant vector containing the nucleic acid molecule or gene expression cassette; a recombinant microorganism containing the promoter or vector; and a method for producing a target product using the recombinant microorganism.

Technical Solution

To achieve the objects of the present disclosure, an aspect of the present disclosure provides a nucleic acid molecule having a promoter activity consisting of any one nucleotide sequence selected from the group consisting of SEQ ID NOS: 1 to 3.

As used in the present disclosure, the term "promoter" refers to an untranslated nucleic acid sequence located upstream of a coding region, which includes a polymerase-binding site and has the activity of initiating transcription of a gene located downstream of a promoter into mRNA, i.e., a DNA domain to which polymerase binds and initiates the transcription of a gene. The promoter may be located at the 5' domain of mRNA transcription initiation domain.

In the present disclosure, the nucleic acid molecules, which have the promoter activity consisting of any one nucleotide sequence selected from the group consisting of SEQ ID NOS: 1 to 3 (i.e., a nucleotide sequence of SEQ ID NO: 1, SEQ ID NO: 2, or SEQ ID NO: 3), were named as SPL1, SPL7, and SPL13, respectively. The nucleic acid molecules having the promoter activity may also be named as promoters, and all of the terms described above may be used in the present disclosure.

The promoter of the present disclosure enables the expression of a target gene, which is operably linked to the nucleic acid molecule having the promoter activity in a target microorganism, and may be used as a general-use promoter.

Additionally, the promoter sequence of the present disclosure may be modified by conventionally-known mutagenesis, e.g., direct evolution, site-directed mutagenesis, etc. Accordingly, the promoter may include without limitation any nucleotide sequence having a homology of 70% or higher, specifically 80% or higher, more specifically 90% or higher, even more specifically 95% or higher, even yet more specifically 98% or higher, and most specifically 99% or higher, to the nucleotide sequence of SEQ ID NO: 1, SEQ ID NO: 2, or SEQ ID NO: 3, and having a similar promoter activity. Additionally, any nucleotide sequence having the above homology, in which part of the sequence is deleted, modified, substituted, or inserted, should be interpreted as being included in the scope of the nucleic acid molecule of the present disclosure as long as the sequence has a promoter activity.

In particular, the expression of "consisting of the nucleotide sequence of SEQ ID NO: 1, SEQ ID NO: 2, or SEQ ID NO: 3" does not exclude the cases of addition, and/or deletion, and/or modification, etc., of a nucleotide that may occur while linking it to a target gene along with the use of a restriction enzyme, when the corresponding promoter is used by linking to the target gene.

Specifically, in addition to the promoter for performing gene transcription, any operator sequence for controlling the transcription, a sequence encoding a suitable mRNA ribosome-binding site, and a sequence for controlling the transcription and translation may be included. For example, the control sequence suitable for prokaryotes may include any operator sequence or ribosome-binding domain, but is not limited thereto. The nucleic acid molecule having the promoter activity of the present disclosure may consist of a sequence for controlling gene expression as described above, according to the necessity by one of ordinary skill in the art.

The nucleic acid molecule, which consists of any one nucleotide sequence selected from the group consisting of SEQ ID NOs: 1 to 3 nucleotide sequences, having a promoter activity may include without limitation a probe which can be prepared from a known gene sequence, for example, any nucleotide sequence which has the promoter activity of the present disclosure by hybridization with a complementary sequence to the entire or partial nucleotide sequence of SEQ ID NOs: 1 to 3 of the present disclosure under a stringent condition.

As used herein, the term "homology" refers to a percentage of identity between two polynucleotides or polypeptide moieties. Sequence homology from one moiety to another may be determined by a known technique in the art. For example, homology may be confirmed using a standard software for calculating parameters such as score, identity, and similarity (specifically BLAST 2.0) or by comparing the sequences via southern hybridization experiments in a defined stringent condition, and the defined appropriate hybridization condition may be determined by a method well-known to one of ordinary skill in the art within the scope of the corresponding technology (e.g., J. Sambrook et al., *Molecular Cloning, A Laboratory Manual,* 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

The "stringent condition" refers to a condition that enables specific hybridization between polynucleotides. This condition is described in detail in references (e.g., J. Sambrook et al., supra). For example, a hybridization condition, where genes with high homology, (e.g., genes with a homology of 80% or higher, specifically 90% or higher, more specifically 95% or higher, even more specifically 97% or higher, and even yet more specifically 99% or higher) are hybridized, and genes with a homology lower than the above are not hybridized; or a washing condition, where washing is performed once, specifically 2 to 3 times, in conditions of salt concentrations and temperature corresponding to a conventional washing condition for southern hybridization (i.e., 60° C., 1×SSC, and 0.1% SDS), specifically 60° C., 0.1× SSC, and 0.1% SDS, more specifically 68° C., 0.1×SSC, and 0.1% SDS, may be included. Although a mismatch between nucleotides may occur due to the stringency of hybridization, it is required that the two nucleic acids have a complementary sequence. The term "complementary" is used to describe the relationship between nucleotide bases which can hybridize with each other. For example, with respect to nucleotide bases, adenosine is complementary to thymine and cytosine is complementary to guanine. Accordingly, the present disclosure may include not only the substantially similar nucleic acid sequences but also isolated nucleic acid fragments which are complementary to the entire sequence. Specifically, the polynucleotide having a homology may be detected using a hybridization condition including the hybridization condition at a Tm value of 55° C. and the conditions described above. Additionally, the Tm value may be 60° C., 63° C., or 65° C., but is not limited thereto and may be appropriately controlled by one of ordinary skill in the art according to the purposes. It is well known that the stringency for the hybridization of polynucleotides depends on the length and degree of complementarity of the polynucleotides and the variables are well-known in the art (see Sambrook et al., supra, 9.50-9.51, 11.7-11.8).

The nucleic acid molecule having a promoter activity of the present disclosure may be isolated or prepared using standard molecular biology techniques. For example, the nucleic acid molecule may be prepared using the standard synthesis technology which uses an automated DNA synthesizer, but the preparation is not limited thereto.

Another aspect of the present disclosure provides a gene expression cassette including the nucleic acid molecule and target gene of the present disclosure.

The nucleic acid molecule of the present disclosure is the same as explained above.

As used herein, the term "gene expression cassette" refers to a unit cassette which includes a promoter and a target gene and thus can express a target gene operably linked to the downstream of the promoter. Such a gene expression cassette may include various factors that can assist efficient expression of the target gene, inside or outside of the cassette. The gene expression cassette may conventionally include a transcription termination signal, a ribosome-binding domain, and a translation termination signal, in addition to the promoter operably linked to the target gene.

As used herein, the term "target gene" refers to a gene encoding a protein to be expressed in a microorganism.

For example, the target gene may be a gene involved in the production of a product selected from the group consisting of saccharides (e.g., psicose or tagatose). L-amino acids (L-lysine, L-valine, etc.), organic acids, enzymes, and a combination thereof, but is not limited thereto. Specifically, the target gene may be a gene encoding a sugar-converting enzyme or an enzyme associated with amino acid biosynthesis, a gene encoding an enzyme associated with reducing power, a gene encoding an enzyme associated with organic acid biosynthesis, or a gene encoding an enzyme associated with the release of a target product, but is not limited thereto. More specifically, the target gene may be a gene encoding psicose epimerase, a gene encoding tagatose epimerase, or a gene encoding tagaturonate epimerase, a gene encoding NADP-dependent glyceraldehyde-3-phosphate dehydrogenase, or a gene encoding a branched-chain amino-acid aminotransferase, but is not limited thereto.

The psicose epimerase may be indicated as ATPE and it refers to psicose-3-epimerase which has an activity of converting fructose into psicose. Additionally, tagaturonate epimerase or tagatose epimerase (hexuronic acid C4-epimerase; Korean Patent No. 10-1550796) may be indicated as UxaE, and it refers to an enzyme which has an activity of converting fructuronate into tagaturonate or converting fructose into tagatose. The NADP-dependent glyceraldehyde-3-phosphate dehydrogenase may be indicated as GapN, and it refers to an enzyme which has an activity of converting into 3-phosphoglycerate using glyceraldehyde 3 phosphate as a substrate. The branched-chain amino-acid aminotransferase may be indicated as IlvE, and it refers to the enzyme of the last step in the biosynthetic pathway of branched-chain amino acids. The sequences of the genes encoding ATPE, UxaE, GapN, and IlvE may be easily obtained through a known database such as the GenBank of the NIH (USA) by one of ordinary skill in the art. The genes encoding ATPE. UxaE, GapN, and IlvE are illustrative target genes that can be operably linked to a nucleic acid molecule having the promoter activity of the present disclosure, and the promoter of the present disclosure can use without limitation any gene, which can be expressed in a microorganism by a general-purpose promoter, as a target gene. As used herein, the term "operably linked" means that the sequence of the above genes and a promoter sequence are functionally linked so that the nucleic acid sequence having the promoter activity of the present disclosure can initiate and mediate the transcription of the target gene. The operable linkage may be prepared using a genetic recombinant technology well-known in the art, and site-specific DNA cleavage and linkage may be prepared using cleavage and linking enzymes, etc., in the art, but is not limited thereto.

Another aspect of the present disclosure provides a recombinant vector, which includes the nucleic acid molecule of the present disclosure or the gene expression cassette of the present disclosure.

The nucleic acid molecule and the gene expression cassette are the same as explained above.

As used herein, the term "vector" is an artificial DNA molecule that possesses a genetic material to enable the expression of a target gene in an appropriate host cell, and specifically, a DNA construct which includes the nucleotide sequence of a gene operably linked to an appropriate regulatory sequence. The regulatory sequence may include, in addition to the promoter capable of initiating transcription, any operator sequence for the regulation of such transcription, a sequence encoding an appropriate mRNA ribosome-binding domain, and a sequence for the regulation of transcription and translation, but is not limited thereto.

The vector used in the present disclosure may not be particularly limited as long as the vector is expressible in a host cell, and the host cell may be transformed using any vector known in the art. Examples of the conventionally-used vector may include natural or recombinant plasmids, cosmids, viruses, and bacteriophages. For example, as a phage vector or cosmid vector, pWE15, M13, λBL3, λBL4, λIXII, λASHII, λAPII, λt10, λt11, Charon4A, Charon21A, etc., may be used; and as a plasmid vector, those based on pBR, pUC, pBluescriptII, pGEM, pTZ, pCL, pET, etc., may be used. The vector to be used in the present disclosure is not particularly limited but any known expression vector may be used. Additionally, the endogenous promoter within the chromosome may be replaced with a nucleic acid molecule having the promoter activity of the present disclosure by a vector for inserting chromosome into a host cell. The insertion of the nucleic acid molecule into chromosome may be carried out by a method well-known in the art, e.g., homologous recombination. For example, pECCG117, pDZ, pACYC177, pACYC184, pCL, pUC19, pBR322, pMW118, pCC1BAC, pCES208, pXMJ19 vectors, etc., may be used, but the vector is not limited thereto. Since the vector of the present disclosure can be inserted into the chromosome via homologous recombination, a selection marker for confirming the insertion into the chromosome may further be included. The selection marker is used for the selection of a transformed cell, i.e., for confirming the insertion of the target nucleic acid molecule, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be selected.

As used herein, the term "transformation" refers to a process for introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all of the essential elements required for self-expression, or in the form of a vector including the expression cassette. The expression cassette or the vector including the polynucleotide may be those which include, for example, a nucleic acid molecule consisting of the nucleotide sequence consisting of SEQ ID NO: 1, SEQ ID NO: 2, or SEQ ID NO: 3 of the present disclosure, having a promoter activity, and may be a vector, to which a target gene is not operably linked. Even in this case, the nucleic acid molecule having the promoter activity may be replaced by the endogenous promoter within the host cell (e.g., a microorganism of the genus *Corynebacterium*) and by homologous recombination. As such, the endogenous gene within the host cell may be expressed.

The method of transformation may include any method which can introduce nucleic acids into a cell, and the transformation may be performed by selecting an appropriate standard technique as known in the art according to the host cell. For example, the method may include electroporation, calcium phosphate ($CaPO_4$) precipitation, calcium chloride ($CaCl_2$) precipitation, microinjection, a polyethylene glycol (PEG) method, a DEAE-dextran method, a cationic liposome method, and a lithium acetate-DMSO method, etc., but is not limited thereto.

Still another aspect of the present disclosure provides a recombinant microorganism which includes a nucleic acid molecule having the promoter activity of the present disclosure, the gene expression cassette, or a recombinant vector including the gene expression cassette.

The nucleic acid molecule having the promoter activity, gene expression cassette, and recombinant vector are the same as explained above.

The gene expression cassette and recombinant vector may be introduced into a microorganism by transformation.

Additionally, the transformation is the same as explained above.

As used herein, the term "microorganism" is a concept including both a wild-type microorganism and a naturally or artificially genetically modified microorganism, and it may be a microorganism having a particular weakened or enhanced mechanism due to insertion of a foreign gene or enhancement or weakening of the activity of an endogenous gene. As used herein, the microorganism may include without limitation any microorganism, in which the nucleic acid molecule having the promoter activity of the present disclosure is introduced and is able to function as a promoter.

Specifically, the microorganism may be a microorganism of the genus *Corynebacterium*, and more specifically, *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, etc. Even more specifically, the microorganism may be *Corynebacterium glutamicum*, but is not limited thereto.

In still another aspect, the present disclosure provides a method of producing a target product, including (a) culturing the recombinant microorganism of the present disclosure in a medium; and (b) recovering a target product from the microorganism or the medium where the microorganism was cultured.

As used herein, the term "target product" may be selected from the group consisting of saccharides (e.g., psicose or tagatose), L-amino acids (e.g., L-lysine, L-valine), organic acids, enzymes, and a combination thereof. The "saccharide" refers to a carbohydrate having a sweet taste, and may be selected from the group consisting of, for example, glucose, fructose, galactose, allulose, tagatose, xylose, lactose, sucrose, and a combination thereof, but is not limited thereto.

The "amino acid" or "L-amino acid" generally refers to a basic constituting unit of a protein in which an amino group and a carboxyl group are bound to the same carbon atom. The amino acid may be selected from the group consisting of, for example, glycine, alanine, valine, leucine, isoleucine, threonine, serine, cysteine, glutamine, methionine, aspartic acid, asparagine, glutamic acid, lysine, arginine, histidine, phenylalanine, tyrosine, tryptophan, proline, and a combination thereof, but is not limited thereto. The organic acids may be organic compounds having an acidic property, for example, those compounds where a carboxy group and a sulfonic group are included therein. Specific examples of the organic acids may include lactic acid, acetic acid, succinic acid, butric acid, palmitic acid, oxalic acid, tartaric acid, citric acid, propionic acid, hexenoic acid, capric acid, caprylic acid, valeric acid, or citric acid, but are not limited thereto. The "enzymes" refer to protein catalysts that mediate chemical reactions occurring in the living organisms, and specifically, enzymes play the role of catalysts lowering the activation energy required for a reaction by forming an enzyme-substrate complex by binding to substrates. For example, some enzymes may be involved in the production of saccharides (e.g., psicose or tagatose), and more specifically, these enzymes may be psicose epimerase, tagatose epimerase, or tagaturonate epimerase, but are not limited thereto. The target products may include any target product which can be produced by the expression of a target gene, which is operably linked to the promoter of the present disclosure, but the target products are not limited thereto.

As used herein, the term "culture" refers to growing a microorganism under appropriately and artificially controlled environmental conditions. In the present disclosure, the culture process may be performed based on appropriate culture media and culture conditions widely-known in the art. Specifically, the culture process may be performed continuously in a batch, a fed batch or a repeated fed batch process, but is not limited thereto.

The media used in the culture must appropriately satisfy the requirements of specific strains. Culture media for the microorganisms of the genus *Corynebacterium* and the genus *Escherichia* are disclosed (e.g., Manual of Methods for General Bacteriology. *American Society for Bacteriology*. Washington D.C. USA, 1981). As a carbon source to be used in the media, sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as gluconic acid, acetic acid, and pyruvic acid may be included, but are not limited thereto. These materials may be used individually or as a mixture. As a nitrogen source to be used, peptone, yeast extract, beef extract, malt extract, corn steep liquor, soybean meal powder, and urea or inorganic compounds such as ammonium sulfate, ammonium chloride, ammonium phosphate, ammonium carbonate, and ammonium nitrate may be included, but the nitrogen source is not limited thereto. The nitrogen source may also be used individually or as a mixture. As a phosphorus source, potassium dihydrogen phosphate or dipotassium hydrogen phosphate or corresponding sodium-containing salts may be used, but the phosphorous source is not limited thereto. In addition, the culture media may include a metal salt such as magnesium sulfate or iron sulfate which is essential for growth. Furthermore, essential materials for growth such as amino acids and vitamins may be used in addition to the above-mentioned materials. Additionally, appropriate precursors may be added to the culture media. Specifically, when an enzyme is produced as a target product, the substrate of the enzyme may be contained in the media. For example, fructose, which can serve as a substrate for psicose epimerase, tagatose epimerase, or tagaturonate epimerase may be included in the media. The above source materials may be adequately fed into the culture in a batch or continuous manner during the culture process. These various culture processes are disclosed, for example, in the reference ("*Biochemical Engineering*" by James M. Lee, Prentice-Hall International Editions, pp 138-176).

The pH of the culture may be adjusted by a proper basic compound such as sodium hydroxide, potassium hydroxide, or ammonia, or an acidic compound such as phosphoric acid or sulfuric acid. Additionally, foaming may be adjusted by an anti-foaming agent such as a fatty acid polyglycol ester. To maintain the aerobic condition of the culture, oxygen or oxygen-containing gas mixtures (e.g., air) may be introduced. The culture temperature may generally be in the range of 20° C. to 45° C., specifically 25° C. to 40° C., but the temperature is not limited thereto and may change according to the culture conditions.

The method of producing a target product of the present disclosure may include a step of recovering the target product from the microorganism of the present disclosure or the media where the microorganism was cultured. The method of producing a target product from the microorganism or the media where the microorganism was cultured is to isolate or recover the target product using an appropriate reaction disclosed in the art. For example, the methods may include a treatment by a protein precipitant (a salting-out method), centrifugation, extraction, ultrasonication, ultrafiltration, dialysis, various chromatography methods such as molecular sieve chromatography (gel filtration), adsorption chromatography, ion exchange chromatography, affinity chromatography, etc., and a combination thereof, but are not limited thereto. The recovery step may include a purification process, and one of ordinary skill in the art may select the process from various purification processes and utilize it as necessary.

Advantageous Effects of the Invention

The novel promoter of the present disclosure may have various activities according to the microorganisms which induce the expression of a target gene. Accordingly, when it is necessary to control the activity of the target gene upon necessity during the production of the target product, the target product can be efficiently produced using the novel promoter of the present disclosure.

BRIEF DESCRIPTION OF DRAWINGS

FIGS. 1A-1B shows the results of GFP assay illustrating the measured strength of novel promoters.

FIGS. 2A-2C shows the results of HPLC confirming the production of psicose.

FIGS. 3A-3B shows the results of HPLC confirming the production of tagatose.

DETAILED DESCRIPTION OF THE INVENTION

Hereinafter, the present disclosure will be described in more detail with reference to the following Examples, etc., to help the understanding of the present disclosure. However, these Examples can be modified in various other forms and the scope of the present disclosure should not be interpreted to be limited by these Examples. The Examples of the present disclosure are provided for the purpose of a full-depth explanation to those who have an average knowledge in the art.

Example 1: Confirmation of Target Gene Expression Induced by a Novel Promoter 1-1. Preparation of Recombinant Vectors Containing Novel Promoter Sequences For the synthesis of a novel promoter capable of inducing the expression of a target gene, various promoter sequences derived from a microorganism of the genus *Corynebacterium* and a microorganism of the genus *Escherichia* were analyzed. Promoters having the nucleotide sequences represented by SEQ ID NOS: 1, 2, and 3 were synthesized and named as SPL1, SPL7, and SPL13, respectively.

Based on SPL1, SPL7, and SPL13 promoters prepared by synthesis as templates, PCR was performed using the primers of SEQ ID NO: 4 and SEQ ID NO: 5 which include KpnI/EcoRV restriction sites [Sambrook et al, *Molecular Cloning, a Laboratory Manual* (1989), Cold Spring Harbor Laboratories]. PCR was performed under the following conditions: denaturation at 94° C. for 5 min; 30 cycles of denaturation at 94° C. for 30 sec, annealing at 60° C. for 30 sec, and extension at 72° C. for 30 sec; and extension at 72° C. for 7 min. As a result, SPL1, SPL7, and SPL13 at a size of about 300 bp were obtained.

The Open Reading Frame (ORF) of the GFP gene was obtained by performing PCR using the pGFPuv vector (Clontech, USA) as a template along with the primers of SEQ ID NO: 6 and SEQ ID NO: 7 which include PstI/EcoRV restriction sites. PCR was performed under the following conditions: denaturation at 94° C. for 5 min; 30 cycles of denaturation at 94° C. for 30 sec, annealing at 55° C. for 30 sec, and extension at 72° C. for 1 min; and extension at 72° C. for 7 min. As a result, the GFP gene fragment (SEQ ID NO: 25) of about 716 bp was obtained.

In the PstI and KpnI restriction sites of a shuttle vector pECCG117 (*Biotechnology letters*, vol 13, No. 10, p. 721-726 (1991), (Korean Patent No. 10-1992-0007401)) which can be expressed in *E. coli* and *Coryne*-form microorganism, each of SPL1. SPL7, and SPL13, which was treated with restriction enzymes KpnI and EcoRV, and the ORF of the GFP gene which was treated with PstI and EcoRV were operably linked to each other using a DNA ligase, and thereby recombinant vectors, in which each of SPL1, SPL7, and SPL13 is linked to GFP, were prepared and they were named as pSPL1-GFP, pSPL7-GFP, and pSPL13-GFP, respectively.

1-2. Preparation of Transformed Strains

The vector pECCG117, the recombinant vectors (pSPL1-GFP, pSPL7-GFP, and pSPL13-GFP) prepared above, and p117-CJ4-GFP, which includes a previously-disclosed promoter pcj4 (Korean Patent No. 10-0620092), were transformed into *Corynebacterium glutamicum* ATCC13032 and *Corynebacterium glutamicum* ATCC13869 by electric pulse method (*Appl. Microbiol. Biotechnol.* (1999) 52: 541-545), respectively, and the transformed strains were obtained in Luria-Bertani (LB) agar plate containing kanamycin (25 mg/L). The strains obtained based on ATCC13032 were named as *Corynebacterium glutamicum* ATCC13032/pECCG117, *Corynebacterium glutamicum* ATCC13032 SPL1-GFP, *Corynebacterium glutamicum* ATCC13032/SPL7-GFP, *Corynebacterium glutamicum* ATCC13032/SPL13-GFP, and *Corynebacterium glutamicum* ATCC13032/CJ4-GFP, respectively. Additionally, the strains obtained based on ATCC13869 were named as *Corynebacterium glutamicum* ATCC13869/pECCG117, *Corynebacterium glutamicum* ATCC13869/SPL1-GFP, *Corynebacterium glutamicum* ATCC13869/SPL7-GFP, *Corynebacterium glutamicum* ATCC13869/SPL13-GFP, and *Corynebacterium glutamicum* ATCC13869/CJ4-GFP, respectively.

The 6 kinds of strains obtained by transformation above, i.e., ATCC13032/SPL7-GFP, ATCC13032/SPL13-GFP, ATCC13032 SPL1-GFP, ATCC13869/SPL7-GFP, ATCC13869/SPL13-GFP, and ATCC13869/SPL1-GFP, were named as CA01-2301, CA01-2302, CA01-2303, CA01-2304, CA01-2305, and CA01-2306, respectively, and then deposited in the Korean Culture Center of Microorganisms (KCCM), an international depositary authority under the Budapest Treaty, on Feb. 17, 2017, with the accession numbers KCCM11971P, KCCM11972P, KCCM11973P, KCCM11974P, KCCM11975P and KCCM11976P.

1-3. Confirmation of Activities of Novel Promoters

For the confirmation of the activities of SPL1, SPL7, and SPL13 promoters, the transformed strains obtained in Example 1-2 (i.e., *Corynebacterium glutamicum* ATCC13032/pECCG117, *Corynebacterium glutamicum* ATCC13032/CJ4-GFP, *Corynebacterium glutamicum* ATCC13032/SPL1-GFP, *Corynebacterium glutamicum* ATCC13032/SPL7-GFP, *Corynebacterium glutamicum* ATCC13032/SPL13-GFP, *Corynebacterium glutamicum* ATCC13869/pECCG117, *Corynebacterium glutamicum* ATCC3869/CJ4-GFP, *Corynebacterium glutamicum* ATCC13869/SPL1-GFP, *Corynebacterium glutamicum* ATCC13869/SPL7-GFP, and *Corynebacterium glutamicum* ATCC13869/SPL13-GFP) were cultured by the method described below and their GFP activities were measured.

The transformed strains were inoculated into each flask containing 25 mL of a culture medium (glucose (20 g), ammonium sulfate (($NH_4)_2SO_4$) (5 g), yeast extract (5 g), urea (1.5 g), $KH_2PO_4$ (4 g), $K_2HPO_4$ (8 g). $MgSO_4.7H_2O$ (0.5 g), biotin (150 µg), thiamine HCl salt (1.5 mg), calcium-pantothenic acid (3 mg), and nicotinamide (3 mg) (based on 1 L of distilled water), pH 7.2) and cultured in a shaking incubator at 30° C. for 20 hours. The bacterial cells were recovered by centrifugation (5,000 rpm, 15 min), washed twice with 50 mM Tris-HCl (pH 8.0) buffer, and suspended in the same buffer. Glass beads were added to the suspension (1.25 g/1.5 mL), and the bacterial cells were disrupted using a bead beater for 6 minutes. Then, the resultant was subjected to centrifugation, (15,000 rpm, 20 minutes) the supernatant was recovered therefrom, and the concentrations of proteins were quantitated by the Bradford method. For an equal amount of bacterial cells extracts, the excited light was irradiated at 488 nm according to a method introduced by Laure Gory et al. (*FEMS Microbiology Letters*, 194, 127-133, 2001), and the emitted light at 511 nm was measured using the LS-50B spectrophotometer (Perkin-Elmer), and thereby the expression level of the GFP gene was measured (Table 1).

TABLE 1

| Strains | Fluorescence Sensitivity |
| --- | --- |
| ATCC13032/pECCG117 | 0.0 |
| ATCC13032/CJ4-GFP | 850.2 |
| ATCC13032/SPL1-GFP | 3197.4 |
| ATCC13032/SPL7-GFP | 3097.7 |
| ATCC13032/SPL13-GFP | 3051.1 |
| ATCC13869/pECCG117 | 0.0 |
| ATCC13869/CJ4-GFP | 921.7 |
| ATCC13869/SPL1-GFP | 3342.3 |
| ATCC13869/SPL7-GFP | 3425.5 |
| ATCC13869/SPL13-GFP | 3287.3 |

As shown in Table 1 above, all of SPL1, SPL7, and SPL13 showed their promoter activities in two different kinds of *Corynebacterium glutamicum* and also showed higher fluorescence sensitivity than the pcj4 promoter, which is known to be a strong promoter. From these results, it was found that SPL1, SPL7, and SPL13 are very strong promoters which can express target genes in *Corynebacterium glutamicum*.

Example 2. Evaluation of the Ability of Producing Target Products 2-1. Evaluation of the Ability of Producing Psicose (1) Preparation of Vectors and Transformed Strains for ATPE Expression Including SPL1 and SPL7 Promoter Sequences Vectors for *Corynebacterium* strains with enhanced expression of ATPE (psicose epimerase derived from *Agrobacterium tumefaciens*) were prepared using SPL1 and SPL7. The Open Reading Frame (ORF) of ATPE gene was amplified by performing PCR (30 cycles of reactions of 30 sec at 94° C., 30 sec at 55° C., and 1 min at 72° C.) using the pET24-ATPE-2 vector (SEQ ID NO: 8) as a template along with the primers of SEQ ID NOS: 9 and 10. The amplified ATPE gene and the pSPL1-GFP and pSPL7-GFP vectors for *Corynebacterium* strains prepared in Example 1 were treated with restriction enzymes EcoRV and PstI, and the ATPE-2 obtained by the PCR was operably linked thereto using the BD In-Fusion kit, and thereby, the pSPL1-ATPE-2 and pSPL7-ATPE-2 vectors for *Corynebacterium* strains were finally prepared.

The thus-prepared pSPL1-ATPE-2 and pSPL7-ATPE-2 vectors were introduced to the ATCC13032 strain by electroporation, and thereby SPL1-ATPE-2 and SPL7-ATPE-2 strains were prepared.

(2) Evaluation of the Ability of Producing Psicose by Transformed Strains

The strains prepared by the above procedure were cultured using the media with the same composition as in Example 1 and their ATPE activities were measured. The ATCC13032/pECCG117 and ATCC13032/CJ4-ATPE-2 strains were used as control groups.

Figure 1A:
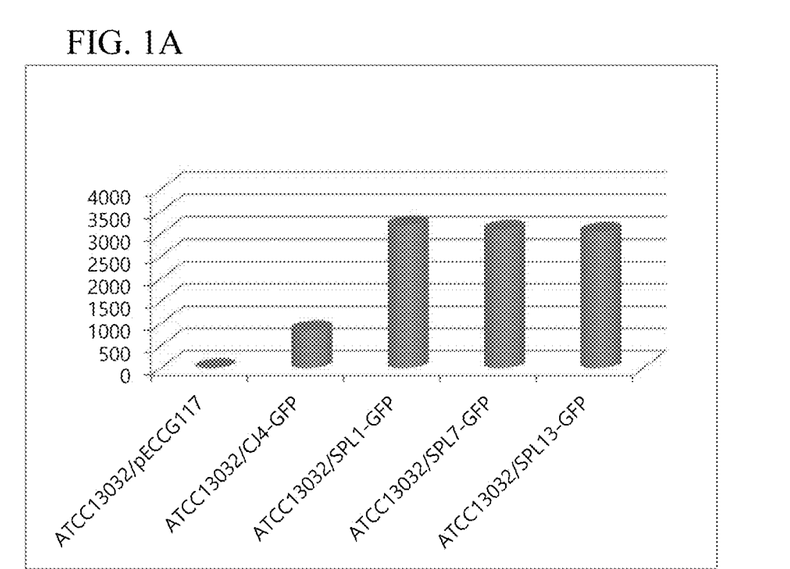
FIG. 1(A) shows the results of GFP assay of novel promoters based on *Corynebacterium glutamicum* ATCC13032.
Figure 1B:
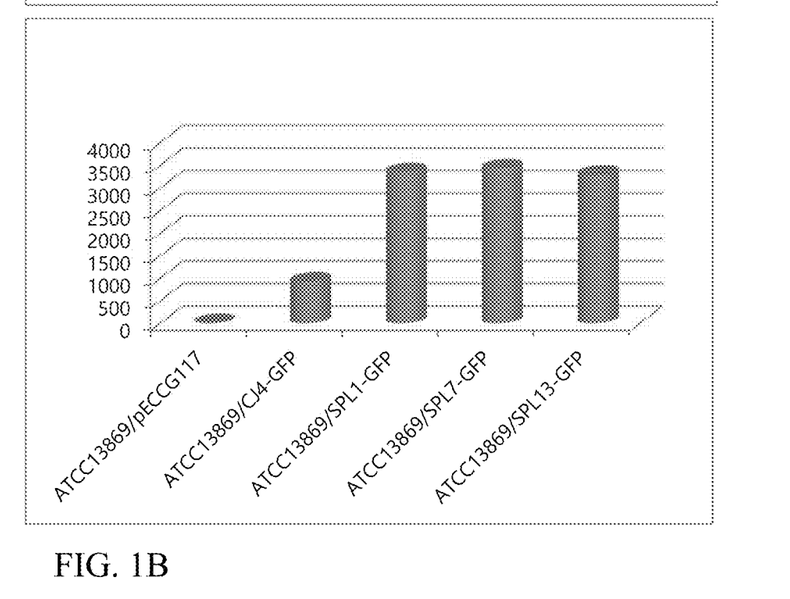
FIG. 1(B) shows the results of GFP assay of novel promoters based on *Corynebacterium glutamicum* ATC13869.

The strains were cultured overnight in a solid LB medium placed in a 30° C. incubator and the overnight culture of each strain was inoculated into a 25 mL medium and cultured in a shaking incubator at 30° C. for 24 hours. The culture was centrifuged and the supernatant was removed. The recovered bacterial bodies were washed with EPPS solution (pH 8.0), and the thus-obtained pellet was dissolved in EPPS solution (pH 8.0). POESA (1 mg/mL) was added thereto, reacted at room temperature for 1 hour, and centrifuged. Then, the resulting pellet obtained by centrifugation was dissolved in EPPS solution (pH 8.0), and a fructose solution (350 g/L) as a substrate was added thereto and reacted at 50° C. for 3 hours, and the reaction was stopped by heat treatment. Then, a supernatant was recovered by centrifugation and the amount of psicose production was measured by HPLC analysis (FIGS. 1(A), 1(B), and 1(C)). The amount of psicose production after reaction was indicated in Table 2 below.

TABLE 2

| Strains | Fructose (g/L) | Psicose (g/L) |
| --- | --- | --- |
| ATCC13032/pECCG117 | 348.7 | 0 |
| ATCC13032/CJ4-ATPE-2 | 329.9 | 18.8 |
| ATCC13032/SPL1-ATPE-2 | 263.2 | 79.2 |
| ATCC13032/SPL7-ATPE-2 | 280.1 | 67.4 |

As shown in Table 2, it was confirmed that the psicose producibilities of *Corynebacterium glutamicum* ATCC13032/SPL1-ATPE-2 and ATCC13032/SPL7-ATPE-2 were improved by 321% and 258%, compared to that of *Corynebacterium glutamicum* ATCC13032/CJ4-ATPE-2, respectively. From the above, it was confirmed that when the SPL1 and SPL7 promoters of the present disclosure were used, the amount of expression of the gene encoding ATPE was increased thus confirming that the ATPE activity was significantly increased.

2-2. Evaluation of the Ability of Producing Tagatose (1) Preparation of Vectors and Transformed Strains for UxaE Expression Including an SPL13 Promoter Sequence Vectors for *Corynebacterium* strains were prepared by cloning the tagatose epimerase gene (UxaE) derived from *Thermotoga neapolitana* using CJ4-GFP, in which GFP is inserted, and SPL13-GFP prepared in Example 1. The Open Reading Frame (ORF) of TN(m) gene was amplified by performing PCR (30 reaction cycles of 30 sec at 94° C., 30 sec at 55° C., and 1 min at 72° C.) using the pET28a-TN(m) vector (SEQ ID NO: 11) as a template along with the primers of SEQ ID NOS: 12 and 13. The amplified TN(m) gene and the CJ4-GFP and SPL13-GFP vectors for *Corynebacterium* strains were treated with restriction enzymes EcoRV and PstI, and then ligated, and thereby, the pCJ4-TN(m) and pSPL13-TN(m) vectors for *Corynebacterium* strains were finally prepared.

The thus-prepared pCJ4-TN(m) and pSPL13-TN(m) vectors were introduced to the ATCC13032 strain by electroporation and thereby ATCC13032/CJ4-TN(m) and SPL13-TN(m) strains were prepared.

(2) Evaluation of the Ability of Producing Tagatose by Transformed Strains

Figure 2A:
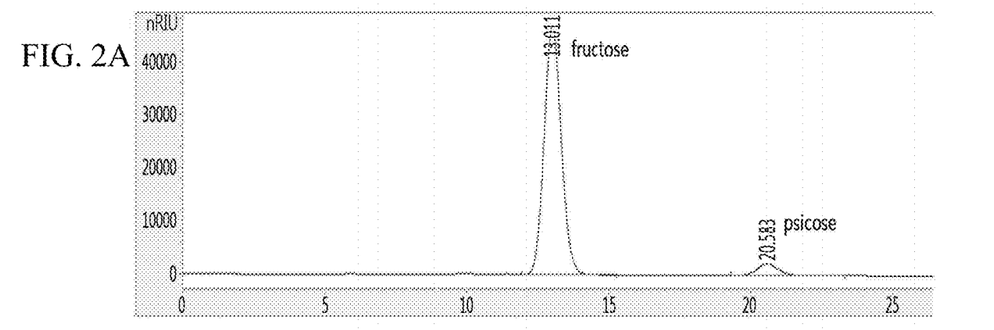
FIG. 2(A) shows the result of the reaction with fructose as a substrate using *Corynebacterium glutamicum* ATCC13032/CJ4-ATPE-2.
Figure 2B:
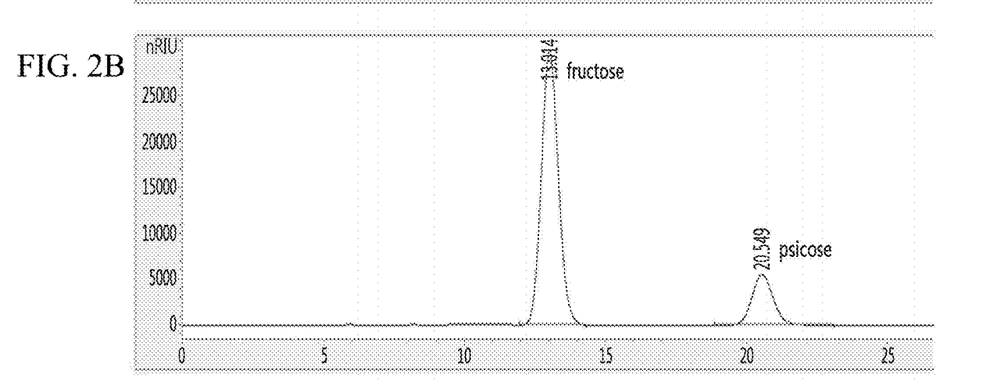
FIG. 2(B) shows the result of the reaction with fructose as a substrate using *Corynebacterium glutamicum* ATCC3032/SPL1-ATPE-2.
Figure 2C:
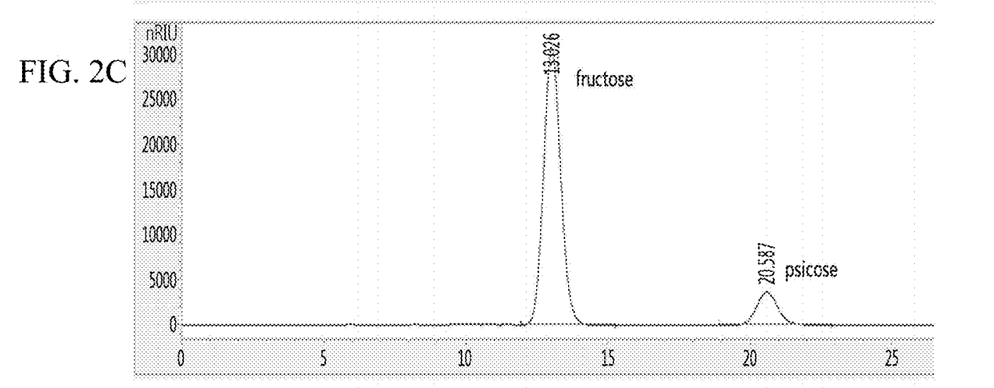
FIG. 2(C) shows the result of the reaction with fructose as a substrate using *Corynebacterium glutamicum* ATCC13032/SPL7-ATPE-2.
Figure 3A:
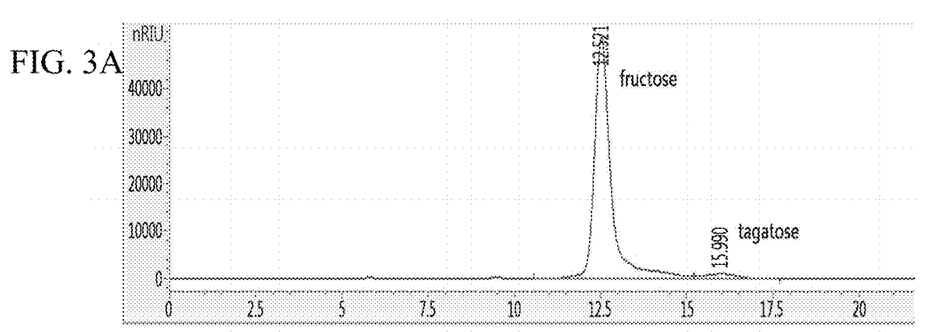
FIG. 3(A) shows the result of the reaction with fructose as a substrate using *Corynebacterium glutamicum* ATCC13032/CJ4-7N(m) and FIG. 3(B) shows the result of the reaction with fructose as a substrate using ATCC13032/SPL13-TN(m).
Figure 3B:
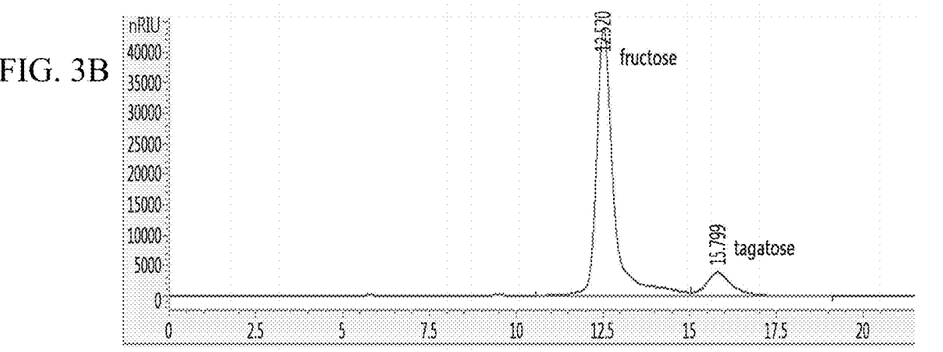

The strains prepared by the above procedure were cultured and pre-treated in the same media and culture conditions described in Example 1 and the strains for activating UxaE were acquired. The evaluation of activity was performed by changing only the amount of substrate, reaction temperature, and time in the same manner as in Example 2-1 (by reacting at 60° C. for 2 hours after adding a fructose solution (100 g/L)). Then, the supernatant was recovered by centrifugation and the amount of tagatose production was measured by HPLC analysis (FIGS. 2(A) and 2(B)). The amount of tagatose production after reaction was indicated in Table 3 below.

TABLE 3

| Strains | Fructose (g/L) | Tagatose (g/L) |
|---|---|---|
| ATCC13032/pECCG117 | 100 | 0 |
| ATCC13032/CJ4-TN(m) | 92.2 | 6.9 |
| ATCCI3032/SPL13-TN(m) | 82.7 | 16.8 |

As shown in Table 3, the tagatose producibility of *Corynebacterium glutamicum* ATCC13032/SPL13-TN(m) was improved by 143% compared to that of *Corynebacterium glutamicum* ATCC13032/CJ4-TN(m). From the above, it was confirmed that when the SPL13 promoter of the present disclosure was used, the amount of expression of the gene encoding UxaE was increased thus confirming that the UxaE activity was significantly increased.

2-3. Evaluation of the Ability of Producing Valine (1) Preparation of pECCG117-SPL7-ilvE Vector and Transformed Strains Including an SPL7 Promoter Sequence For the confirmation of L-valine producing ability as an example of L-amino acids, pECCG11?-CJ7-ilvE and pECCG117-SPL7-ilvE vectors were prepared as follows, so as to enhance the enzyme activity of ilvE (NCgl2123), which encodes a branched-chain amino-acid aminotransferase, which is a major gene for valine biosynthesis. Specifically, as a result of performing PCR (30 reaction cycles of 30 sec at 94° C., 30 sec at 55° C., and 1 min at 72° C.) using the ATCC14067 chromosome as a template along with the primers of SEQ ID NOS: 14 and 15, a PCR fragment with a size of about 1104 bp, which has an EcoRV restriction site at 5' end and a PstI restriction site at 3' end of the NCgl2123 gene, was amplified. The thus-obtained PCR fragment was purified and mixed with pECCG117-CJ7-GFP (Korean Patent No. 10-0620092) and pECCG117-SPL7-GFP, which were treated with EcoRV and PstI restriction enzymes, respectively, and vectors were prepared using the In-fusion cloning Kit. The thus-prepared vectors were named as pECCG117-CJ7-ilvE and pECCG117-SPL7-ilvE, respectively.

SEQ ID NO: 14
5' GAGATCAAAACAGATATCATGACGTCATTAGAGTTC 3'

SEQ ID NO: 15
5' ATCCCCCGGGCTGCAGTTAGCCAACCAGTGGGTA 3'

The thus-prepared recombinant vectors of pECCG117-CJ7-ilvE and pECCG117-SPL7-ilvE, and the pECCG117 vector were transformed into a valine-producing strain, *Corynebacterium glutamicum* KCCM1201P (Korean Patent No. 10-1117022), by an electric pulse method, and the transformed strains were obtained in a LB agar plate containing kanamycin (25 mg/L). The thus-obtained strains were named as KCCM11201P/pECCG117, KCCM11201P/CJ7-ilvE, and KCCM11201P/SPL7-ilvE, respectively.

(2) Evaluation of the Ability of Producing Valine by Transformed Strains

The ability of producing L-valine by the 3 different kinds of transformed strains was analyzed by culturing as described below.

Each of the strains in an amount of a platinum loop was inoculated into a 250 mL corner-baffle flask containing 25 mL of a production medium and cultured in a shaking incubator (200 rpm) at 30° C. for 72 hours. Upon completion of the cultivation, the concentration of L-valine in each culture was analyzed by HPLC (SHIMADZU LC-20AD).

<Production Medium (pH 7.2)>

Glucose (50 g), $(NH_4)_2SO_4$ (20 g), Corn Steep Solids (20 g), $KH_2PO_4$ (1 g), $MgSO_4.7H_2O$ (0.5 g), Biotin (200 µg) (based on 1 L of distilled water)

The above cultivation and analysis were performed repeatedly, and the analyzed L-valine concentrations are shown in Table 4 below.

TABLE 4

| | Strains | L-valine (g/L) | | | |
|---|---|---|---|---|---|
| | | Batch 1 | Batch 2 | Batch 3 | Average |
| Control | KCCM11201P/pECCG117 | 2.7 | 2.9 | 2.9 | 2.8 |
| 1 | KCCM11201P/CJ7-ilvE | 3.1 | 3.2 | 3.4 | 3.2 |
| 2 | KCCM11201P/SPL7-ilvE | 3.9 | 4.0 | 3.8 | 3.9 |

As shown in Table 4, it was confirmed that the ability of producing valine by the KCCM11201P/SPL7-ilvE strain, where the promoter of the present disclosure is introduced, was improved by 21.8% compared to that of the *Corynebacterium glutamicum* KCCM11201P/CJ7-ilvE, where a known promoter is introduced, and additionally, it was improved by 39.2% compared to that of the control group, KCCM11201P/pECCG117. From the above results, it was confirmed that the SPL7 promoter enhanced the expression of the ilvE gene thereby significantly increasing the activity of the enzyme encoded by the corresponding gene.

2-4. Evaluation of the Ability of Producing Lysine (1) Preparation of pDZTn-SPL13-gapN1 Vector and Transformed Strains Including an SPL13 Promoter Sequence For the confirmation of L-lysine producing ability as a representative example of L-amino acids, vectors were prepared as follows so as to enhance the enzyme activity of the NADP-dependent glyceraldehyde-3-phosphate dehydrogenase (GapN), which is derived from known *Streptococcus mutants*.

For the insertion into a transposable gene NCgl2392 in a microorganism of the genus *Corynebacterium*, PCR (30 reaction cycles of 30 sec at 94° C., 30 sec at 55° C., and 1 min at 72° C.) was performed using the chromosome of the wild-type *Corynebacterium glutamicum* ATCC13032 as a template, along with the following primers of SEQ ID NO: 16, SEQ ID NO: 17. SEQ ID NO: 18, and SEQ ID NO: 19, based on the NIH Genbank of the NIH (USA), and as a result, fragments including the 5'end and the 3' end of NCgl2392 gene were amplified. As a result of performing PCR (30 reaction cycles of 30 sec at 94° C., 30 sec at 55° C., and 2 min at 72° C.) using the pECCG122-Pcj7-gapN1 vector (Korean Patent No. 10-1182033) along with the following primers of SEQ ID NO: 20 and SEQ ID NO: 21, Pcj7-gapN1 was amplified. As a result of performing PCR (30 reaction cycles of 30 sec at 94° C., 30 sec at 55° C., and 1 min at 72° C.) using the pECCG122-Pcj7-gapN1 vector and the SPL13-GFP vector prepared in Example 1, along with the following primers of SEQ ID NO: 22, SEQ ID NO: 23, SEQ ID NO: 24, and SEQ ID NO: 21, SPL13 and gapN genes were amplified, respectively, and these genes were cloned into the pDZ vector (Korean Patent No. 0924065), which is not replicable in *Corynebacterium glutamicum*, along with the NCgl2392 gene fragments prepared above, and thereby pDZTn-Pcj7-gapN1 and pDZTn-SPL13-gapN1 vectors were prepared.

```
                                          SEQ ID NO: 16
5' ATCCTCTAGAGTCGACCAAATGCTCCAACCGTCCGT 3'

SEQ ID NO: 17
5' CTCGAGGAACTCATTCCTTCTGCTCG 3'

SEQ ID NO: 18
5' TCTAGAACTAGTGGGCCCGACATCTAATAACCGGGCAG 3'

SEQ ID NO: 19
5' ATGCCTGCAGGTCGACGCAGACGCACTCGACTACAC 3'

SEQ ID NO: 20
5' GAATGAGTTCCTCGAGAGAAACATCCCAGCGCTACT 3'

SEQ ID NO: 21
5' GCCCACTAGTTCTAGATTATTTGATATCAAATACGA 3'

SEQ ID NO: 22
5' GAATGAGTTCCTCGAGGGCGCTTCATGTCAACAATC 3'

SEQ ID NO: 23
5' ATTGTTTTGTCATATGTGTTTTGATCTCCTCCAATA 3'

SEQ ID NO: 24
5' CATATGACAAAACAATATAAAAA 3'
```

Each of the above vectors (pDZTn-Pcj7-gapN1 and pDZTn-SPL13-gapN1) was transformed using the KCCM11016P strain with enhanced ability of producing lysine (the microorganism was disclosed as KFCC10881, re-deposited to an international depositary authority under the Budapest treaty, and assigned an accession number of KCCM11016P; Korean Patent No. 10-0159812) as a parent strain, by the electric pulse method (*Appl. Microbiol. Biotechnol.* (1999) 52: 541-545), and transformed strains were obtained in a selective medium containing 25 mg/L of kanamycin. In order to select colonies in which the gapN gene was inserted in the genome by secondary recombination process (crossover), those colonies where the Pcj7-gapN1 and SPL13-gapN1 genes are inserted, respectively, were obtained using primer pairs of SEQ ID NOS: 20 and 21 and SEQ ID NOS: 21 and 22. The thus-obtained colonies were named as KCCM11016P/CJ7-gapN1 and KCCM11016P/SPL13-gapN1, respectively.

(2) Evaluation of the Ability of Producing Lysine by Transformed Strains

The ability of producing L-lysine by the 3 different kinds of transformed strains was analyzed by culturing as described below.

Each of the strains was inoculated into a 250 mL corner-baffle flask containing 25 mL of a seed medium and cultured in a shaking incubator (200 rpm) at 30° C. for 20 hours.

Then, 1 mL of the seed culture was inoculated into a 250 mL corner-baffle flask containing 24 mL of a production medium and cultured in a shaking incubator (200 rpm) at 30° C. for 72 hours. The concentration of L-lysine in each culture was analyzed by HPLC (SHIMADZU, LC-20AD).

<Seed Medium (pH 7.0)>

Glucose (20 g). Peptone (10 g), Yeast Extract (5 g). Urea (1.5 g), $KH_2PO_4$ (4 g), $K_2HPO_4$ (8 g), $MgSO_4.7H_2O$ (0.5 g), Biotin (100 μg), Thiamine HCl (1000 μg), Calcium-Pantothenic Acid (2000 μg), Nicotinamide (2000 μg) (based on 1 L of distilled water)

<Production Medium (pH 7.0)>

Glucose (100 g), $(NH_4)_2SO_4$ (40 g), Soybean Protein (2.5 g), Corn Steep Solids (5 g), Urea (3 g), $KH_2PO_4$ (1 g), $MgSO_4.7H_2O$ (0.5 g), Biotin (100 μg), Thiamine HCl salt (1000 μg), Calcium-Pantothenic Acid (2000 μg), Nicotinamide (3000 μg), and $CaCO_3$ (30 g) (based on 1 L of distilled water)

The above cultivation and analysis were performed repeatedly, and the analyzed L-lysine concentrations are shown in Table 5 below.

TABLE 5

| | | L-lysine (g/L) | | | |
|---|---|---|---|---|---|
| | Strains | Batch 1 | Batch 2 | Batch 3 | Average |
| Control | KCCM11016P | 42.3 | 43.1 | 41.2 | 42.2 |
| 1 | KCCM11016P/CJ7-gapN1 | 47.6 | 49.1 | 49.2 | 48.3 |
| 2 | KCCM11016P/SPL13-gapN1 | 51.0 | 51.5 | 52.9 | 51.8 |

As shown in Table 5, it was confirmed that the ability of producing lysine by the KCCM1016P/SPL13-gapN1 strain, where the promoter of the present disclosure is introduced, was improved by 7.2% compared to that of the *Corynebacterium glutamicum* KCCM11016P/CJ7-gapN1, where a known promoter is introduced, and additionally, it was improved by 22.7% compared to that of the control group, KCCM11016P. From the above results, it was confirmed that the SPL13 promoter enhanced the expression of the gapN1 gene thereby significantly increasing the activity of the enzyme encoded by the corresponding gene.

Summarizing the above results, the SPL1, SPL7, and SPL13 promoters of the present disclosure can significantly enhance the expression of a target gene in a recombinant microorganism, compared to the conventional known promoters. Accordingly, the promoters of the present disclosure can not only provide an effective expression system but also be effectively used in various industrial fields for high-yield production of target products, such as saccharides, functional materials, and amino acids.

The invention claimed is:

1. A nucleic acid molecule having a promoter activity consisting of any one of the nucleotide sequence selected from the group consisting of SEQ ID NOS: 1 to 3.

2. A gene expression cassette comprising the nucleic acid molecule of claim 1 and a target gene.

3. A recombinant vector comprising the nucleic acid molecule of claim 1.

4. A recombinant microorganism of the genus *Corynebacterium* comprising the nucleic acid molecule of claim 1.

5. The recombinant microorganism according to claim 4, wherein the microorganism of the genus *Corynebacterium* is *Corynebacterium glutamicum* or *Corynebacterium ammoniagenesis*.

6. A method of producing a target product, comprising:
(a) culturing the recombinant microorganism of claim 4 in a medium; and
(b) recovering a target product from the microorganism or the medium.

7. The method according to claim 6, wherein the target product is psicose, tagatose, or an amino acid.

8. A recombinant vector comprising the gene expression cassette of claim 2.

9. A recombinant microorganism of the genus *Corynebacterium* comprising the recombinant vector of claim 3.

10. A recombinant microorganism of the genus *Corynebacterium* comprising the recombinant vector of claim 8.

11. The recombinant microorganism according to claim 9, wherein the microorganism of the genus *Corynebacterium* is *Corynebacterium glutamicum* or *Corynebacterium ammoniagenesis*.

12. The recombinant microorganism according to claim 10, wherein the microorganism of the genus *Corynebacterium* is *Corynebacterium glutamicum* or *Corynebacterium ammoniagenesis*.

13. A method of producing a target product, comprising:
(a) culturing the recombinant microorganism of claim 9 in a medium; and
(b) recovering a target product from the microorganism or the medium.

14. A method of producing a target product, comprising:
(a) culturing the recombinant microorganism of claim 10 in a medium; and
(b) recovering a target product from the microorganism or the medium.

15. The method according to claim 13, wherein the target product is psicose, tagatose, or an amino acid.

16. The method according to claim 14, wherein the target product is psicose, tagatose, or an amino acid.

* * * * *

UNITED STATES PATENT AND TRADEMARK OFFICE
CERTIFICATE OF CORRECTION

PATENT NO. : 10,584,338 B2
APPLICATION NO. : 16/327581
DATED : March 10, 2020
INVENTOR(S) : Young Mi Lee et al.

It is certified that error appears in the above-identified patent and that said Letters Patent is hereby corrected as shown below:

In the Specification

At Column 1, Line numbers 38 and 42, please change "ammoniagenesis" to --ammoniagenes--;

In the Claims

At Column 27, Claim 5, Line numbers 30 and 31, please change "ammoniagenesis" to --ammoniagenes--;

At Column 28, Claim 11, Line numbers 22 and 23, please change "ammoniagenesis" to --ammoniagenes--;

At Column 28, Claim 12, Line number 27, please change "ammoniagenesis" to --ammoniagenes--.

Signed and Sealed this
Twenty-first Day of February, 2023

Katherine Kelly Vidal
*Director of the United States Patent and Trademark Office*